(12) United States Patent  
Kosik et al.

(10) Patent No.: US 9,242,041 B2  
(45) Date of Patent: Jan. 26, 2016

(54) METHOD AND APPARATUS FOR CANCER TREATMENT

(71) Applicant: Quantum Cure, Inc., State College, PA (US)

(72) Inventors: Alex Kosik, Manassas, VA (US); Wes Hymer, State College, PA (US); Max I. Fomitchev-Zamilov, Sate College, PA (US)

(73) Assignee: QUANTUM CURE, INC., State College, PA (US)

( * ) Notice: Subject to any disclaimer, the term of this patent is extended or adjusted under 35 U.S.C. 154(b) by 402 days.

(21) Appl. No.: 13/919,613

(22) Filed: Jun. 17, 2013

(65) Prior Publication Data

US 2014/0371665 A1    Dec. 18, 2014

(51) Int. Cl.
| | |
|---|---|
| *A61M 5/158* | (2006.01) |
| *A61B 18/14* | (2006.01) |
| *A61N 1/30* | (2006.01) |
| *A61N 1/04* | (2006.01) |
| *A61B 18/00* | (2006.01) |
| *A61B 19/00* | (2006.01) |
| *A61M 5/142* | (2006.01) |

(52) U.S. Cl.
CPC ............ *A61M 5/158* (2013.01); *A61B 18/1477* (2013.01); *A61N 1/306* (2013.01); *A61B 2018/00613* (2013.01); *A61B 2018/1425* (2013.01); *A61B 2019/5276* (2013.01); *A61M 5/142* (2013.01); *A61M 2205/055* (2013.01); *A61N 1/0412* (2013.01); *A61N 1/0428* (2013.01)

(58) Field of Classification Search
CPC ................... A61B 18/1477; A61B 2019/5276; A61B 2018/1425; A61B 2018/00613; A61M 5/158; A61M 2205/055; A61M 5/142; A61N 1/306; A61N 1/0428; A61N 1/0412
USPC ......... 604/22, 65–67, 131, 151; 128/DIG. 12, 128/DIG. 13
See application file for complete search history.

(56) References Cited

U.S. PATENT DOCUMENTS

| | | | |
|---|---|---|---|
| 6,622,731 B2* | 9/2003 | Daniel | A61B 18/1477 128/898 |
| 7,108,696 B2* | 9/2006 | Daniel | A61B 18/1477 606/41 |

(Continued)

FOREIGN PATENT DOCUMENTS

SU    1685473 A1    10/1991

OTHER PUBLICATIONS

International Search Report and Written Opinion issued in International Application No. PCT/US2014/042767 mailed on Jun. 17, 2014.

*Primary Examiner* — Manuel Mendez  
(74) *Attorney, Agent, or Firm* — Oliff PLC

(57) ABSTRACT

An apparatus for treating solid tumors having at least one hollow needle having at least one perforation, at least one ground electrode, a pump for delivering a chemotherapeutic agent through the perforation in the hollow needle, one or more power supplies connected to the hollow needle and the ground electrode capable of delivering a pulse of alternating current between the hollow needle and the ground electrode of at least 1000 volts and no more than 1 millisecond duration, a direct current between the hollow needle and the ground electrode between about 1 mA and 100 mA, and a second alternating current having a frequency range between about 1 MHz and 1000 MHz.

14 Claims, 5 Drawing Sheets

(56) References Cited

U.S. PATENT DOCUMENTS

| | | | |
|---|---|---|---|
| 2002/0133148 A1* | 9/2002 | Daniel | A61B 18/1477 606/34 |
| 2004/0059328 A1* | 3/2004 | Daniel | A61B 18/1477 606/41 |
| 2004/0200731 A1* | 10/2004 | Sullivan | C02F 1/48 205/628 |
| 2007/0112342 A1 | 5/2007 | Pearson et al. | |
| 2010/0331758 A1 | 12/2010 | Davalos et al. | |
| 2014/0074203 A1* | 3/2014 | Na et al. | A61B 18/1477 607/116 |

* cited by examiner

METHOD AND APPARATUS FOR CANCER TREATMENT

TECHNICAL FIELD

This invention relates to methods and devices for treating cancerous tumors.

BACKGROUND OF THE INVENTION

There have been a number of examples of instruments and methods for treating cancerous tumors. While these prior art methods and apparatus have been shown to partially or entirely eliminate cancerous tumors within a patient's tissue and thereby improve the patient's condition, unfortunately, none have proven to completely eliminate the cancerous cells in all cases, or to otherwise provide a complete cure. Further, many of these prior art methods will adversely impact healthy tissues and cells within the patient in addition to the cancerous cells. Thus, there is a need for improved methods and apparatus for treating cancerous tumors.

SUMMARY OF THE INVENTION

The present disclosure is directed to a method and apparatus for treating cancerous tumors. The apparatus includes at least one hollow needle having at least one perforation, at least one ground electrode, a pump for delivering a chemotherapeutic agent through the perforation in the hollow needle, one or more power supplies connected to the hollow needle and the ground electrode capable of delivering three separate wave forms between the hollow needle and the ground electrode.

According to various aspects, an exemplary apparatus for treating cancerous tumors operates by inserting the hollow needle into a patient's tissue such that the perforation in the hollow needle is on one side of a tumor in the tissue. The ground electrode is placed either inside the tumor or on the opposite side of the tumor from the hollow needle. The ground electrode may also constitute a needle, which may also be inserted into the tumor or into the patient's tissue adjacent to the tumor, depending upon the location of the tumor. A chemotherapeutic agent is then introduced into the patient's tissue by using the pump to pump the chemotherapeutic agent through the perforation in the hollow needle. In this manner, a chemotherapeutic agent is introduced adjacent to the cancerous cells or cancerous tumor that is to be killed.

The hollow needle and the ground electrode are connected to one or more power supplies to create an electrical circuit. Preferably, the formation of the circuit occurs simultaneously with the introduction of the chemotherapeutic agent, however, the invention should not be limited as to the timing of these events. Those having ordinary skill in the art will recognize that the formation of the circuit will have therapeutic benefits regardless of the relative timing of the circuit with respect to the introduction of the chemotherapeutic agent into the patient's tissue.

The power supplies are used to create three separate waveforms between the hollow needle and the ground electrode.

The first wave form is a low voltage direct current (DC) between about 1 mA and 100 mA. The application of the DC will cause the chemotherapeutic agent to move from the hollow electrode to the ground electrode by electrophoresis. By positioning the hollow and ground electrodes on opposite sides of the cancerous tumor that is to be treated, the chemotherapeutic agent is delivered precisely to the cancerous cells that are to be treated, thereby avoiding to the maximum extent possible the exposure of healthy cells surrounding the tumor.

The second waveform is a high voltage direct current (DC) between about 1 kV and 10 kV. The application of this second DC waveform will cause the heating and electroporation of the cells in between the hollow electrode and the ground electrode. By positioning the hollow and ground electrodes on opposite sides of the cancerous tumor that is to be treated, the electroporation is delivered precisely to the cancerous cells that are to be treated, thereby avoiding to the maximum extent possible the electroporation of healthy cells surrounding the tumor.

In another aspect of this electrical circuit, the power supply is operated to form an alternating current (AC). This alternating current has a frequency range between about 1 MHz and 1000 MHz. One or more pulses of the alternating current between the hollow needle and the ground electrode of amplitude of at least 1000 volts and no more than 1 millisecond duration will cause electroporation cells. By positioning the hollow and ground electrodes on opposite sides of the cancerous tumor that is to be treated, the pulses are delivered precisely to the cancerous cells that are to be treated, thereby causing electroporation of these cancerous cells and avoiding to the maximum extent possible the electroporation of healthy cells surrounding the tumor.

Preferably, but not meant to be limiting, the hollow needle of the present invention is housed in a manipulator housing having a servo drive for injecting the needle into a tissue operated by a trigger on the manipulator. In this arrangement, an operator is provided precise control of the location and depth of the insertion of the hollow needle into the patient's tissue. The manipulator housing may further have an ultrasound imager, thereby allowing the operator to see the tumor and the relative location of the needle in real time, as the needle is inserted into the patient's tissue. Both the servo and the ultrasound imager are preferably connected to a computer, thereby allowing processing of the ultrasound image and projection of the image to a monitor, and allowing precise control of the servo by the computer.

BRIEF DESCRIPTION OF THE DRAWINGS

The following detailed description of the embodiments of the invention will be more readily understood when taken in conjunction with the following drawings, wherein.

DETAILED DESCRIPTION OF THE PREFERRED EMBODIMENTS

Figure 1:
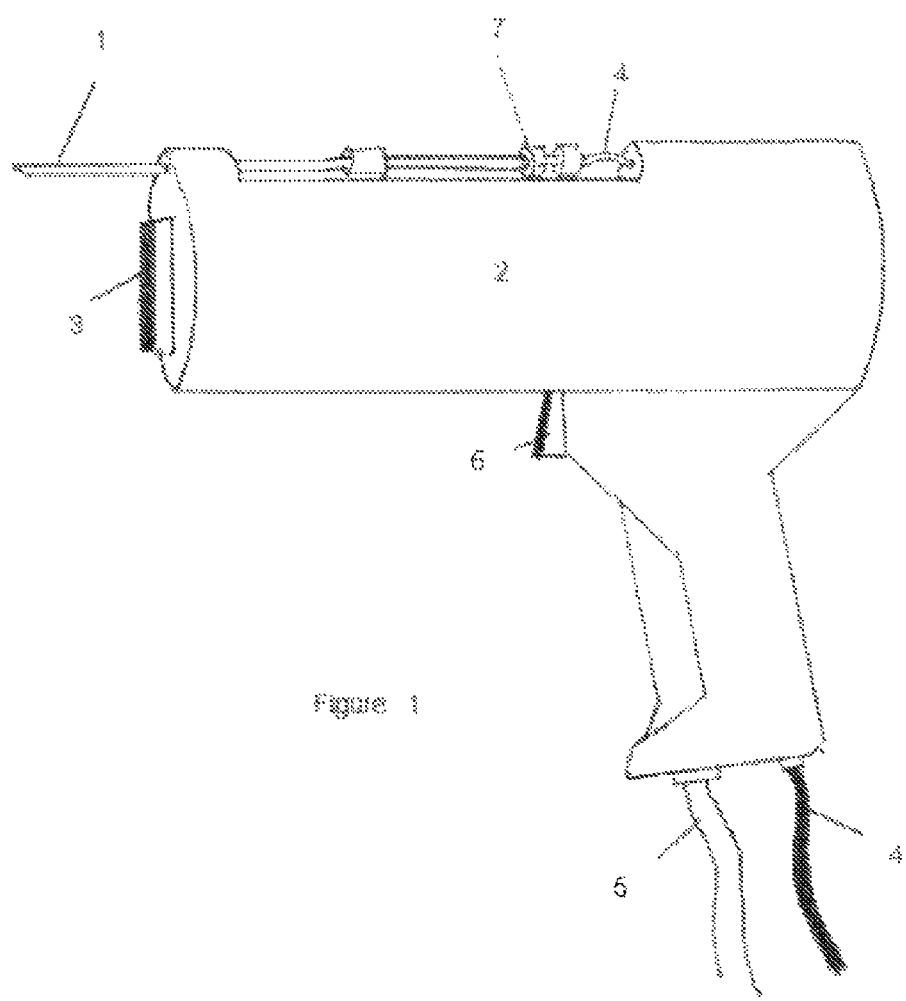
FIG. 1 is an illustration of the manipulator portion of the apparatus of the present invention.

For the purposes of promoting an understanding of the principles of the invention, reference will now be made to the embodiments illustrated in the drawings and specific language will be used to describe the same. It will nevertheless be understood that no limitations of the inventive scope is thereby intended, as the scope of this invention should be evaluated with reference to the claims appended hereto. Alterations and further modifications in the illustrated devices, and such further applications of the principles of the invention as illustrated herein are contemplated as would normally occur to one skilled in the art to which the invention relates.

The present invention uses a combination of hyperthermia, chemotherapy and irreversible electroporation (IRE) to take advantage of their synergism and delivers them sequentially and/or simultaneously to the local tumor area using a relatively simple device, which may thereby avoid surgery and extensive hospital treatment.

As used herein, hyperthermia is the distribution of heat energy into tumor tissue. While not meant to be limiting, hyperthermia is typically not homogeneous because tumor histology shows heterogeneity. Preferably, but not meant to be limiting, hyperthermia as practiced by the present invention heats at least a portion of the tumor tissue to at or slightly above 42° C., where tumor blood flow decreases and microenvironments are hypoxic and of low pH.

As used herein, chemotherapy with electrophoresis means the use of an electrical field to deliver a chemotherapeutic agent to a tumor. In the present invention, a chemotherapeutic agent is delivered into the vicinity of the tumor by positive pressure through a hollow needle, and then a DC current-driven electrophoresis electrode is used to drive the chemotherapeutic agent inside the tumor.

As used herein, irreversible electroporation (IRE) is defined as the application of short (microsecond to millisecond) high voltage electric pulses that permanently alter the cell's transmembrane potential, thereby changing cell homeostasis and causing cell death. While not meant to be limiting, the "cut-off" point between reversible and irreversible electroporation is about 600 V/cm, depending upon pulse frequency/number/mode of delivery. Also while not meant to be limiting, increasing the average pore size in cell membranes to 250 nm is generally sufficient to cause irreversible electroporation (IRE).

The QC prototype consists of four elements:
1) a chemotherapeutic delivery system including a power source for electrophoretic transport of the chemotherapeutic agent,
2) a power source for UHF field generation,
3) a power source for IRE ablation, and
4) a pistol for their application within or around the tumor.

The power source for each of electrophoretic transport of the chemotherapeutic agent, UHF field generation, and IRE ablation may be combined into a single power source.

In a clinical application, an exemplary method of the present disclosure begins by delivering a local anesthetic to the tumor area using conventional means. The ground electrode(s) of the exemplary apparatus are then inserted into the patient's tissue.

The UHF electrodes are then activated inside the needles to heat the tumor tissues to approximately 45° C. for a duration of between 0.5 and 1 minute. Sensors may be provided in each electrode to calculate temperatures around and inside the tumor, and the power supply may be configured to automatically shut off the power supply if temperature exceeds a certain threshold, for example, 45° C.

Once temperature has achieved a certain threshold, for example, and not meant to be limiting, 40° C., the pump begins delivering a chemotherapeutic agent through needle(s) surrounding the tumor. Preferably, this delivery process continues for about 5 minutes. Also preferably, but not meant to be limiting, the chemotherapeutic agent is delivered in 60 second "pulses" to help achieve even saturation. As will be evident to those having ordinary skill in the art, the chemotherapeutic agent may be a combination of one or more molecules that are shown to kill cancer cells. As such, as used herein, the term "chemotherapeutic agent" should be understood to encompass chemotherapeutic agents either alone or in combination with other chemotherapeutic agents.

Upon temperature stabilization at a predetermined threshold, for example but not meant to be limiting, 44° C., and initial drug saturation of the tumor, the IRE generator is then activated, and irreversible electroporation begins using the hollow needle and the ground electrode. This results in non-thermal ablation, and the effect on local healthy tissues is minimized because the ground electrode is inside the tumor.

Immediately upon IRE electrode activation, the DC current is imposed between the hollow electrode and the ground electrode, thereby electrophoretically driving the drug through tissues and towards the ground electrode. This step allows drug penetration deep into tumor tissue. Preferably, both IRE and UHF electrical fields are imposed for the remaining duration of the procedure, for example, between 7 and 10 minutes.

Upon removal of the needle electrode, the injection site is sanitized and a surgical bandage is applied. Preferably, the central puncture (where the hollow electrode was installed) is not closed, but a sterile drainage tube is inserted to enable passive drainage. The drainage tube, in place for about 3-5 days, for example, helps ensure removal of necrotic debris. Antibiotic is administered to the patient to prevent infection. The entire procedure can be repeated if a biopsy of the treated area reveals residual viable tumor.

FIG. 1 illustrates the manipulator portion of an exemplary device used in an exemplary embodiment of the present disclosure. As shown in FIG. 1, the device includes a hollow needle 1, which is contained within a manipulator 2. An ultrasound imager 3 is mounted on the front of the manipulator 2. A fluid line 4 is provided to allow the flow of the chemotherapeutic agent from the pump (not shown in this figure) through the hollow needle 1. An electrical connection 5 provides power from the power supply (not shown in this figure) to the hollow needle 1 and also provides communication between the computer (not shown in this figure), the servo drive 7, and the ultrasound imager 3. The trigger 6 is used to activate the servo drive 7 to inject the hollow needle 1 into a patient.

Figure 2:
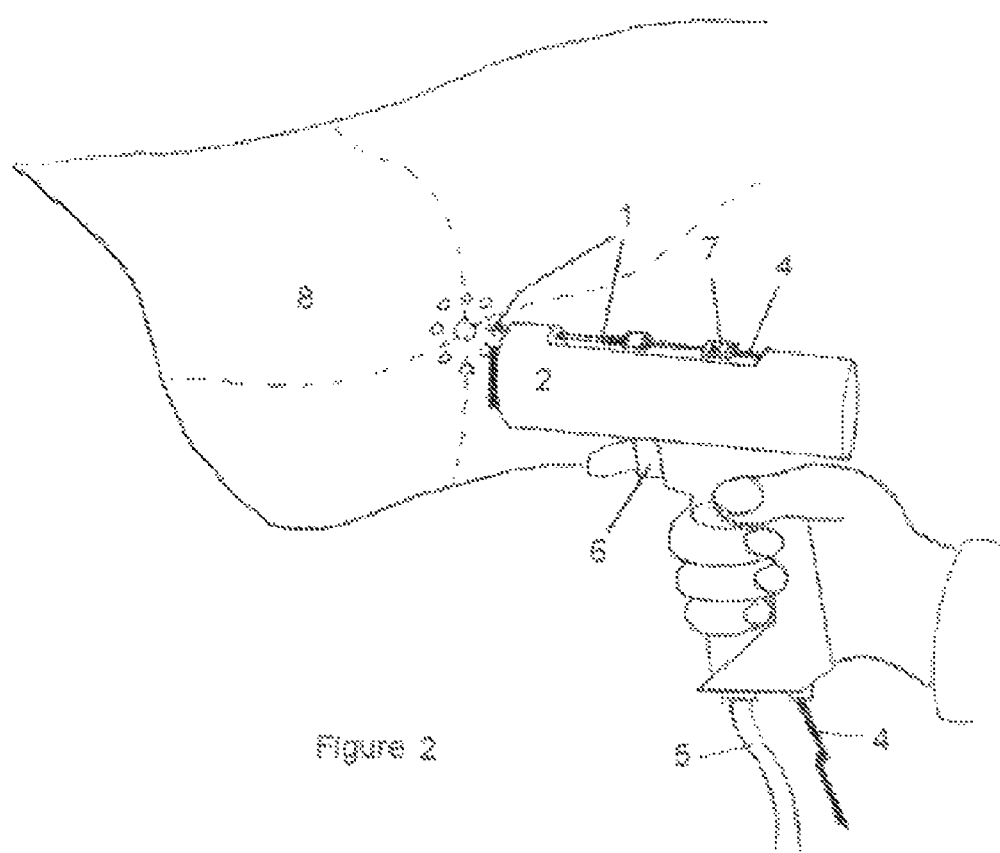
FIG. 2 is an illustration of the manipulator portion of the apparatus of the present invention being used to deliver treatment to a patient.

FIG. 2 shows the manipulator 2 of FIG. 1 in operation. As shown in the figure, the hollow needle 1 contained within the manipulator 2 is inserted into a patient 8. The ultrasound imager 3 is flush with patient 8 thereby allowing the operator 9 to have an accurate, real time image of the tumor (not shown in this figure) inside of the patient 8.

Figure 3:
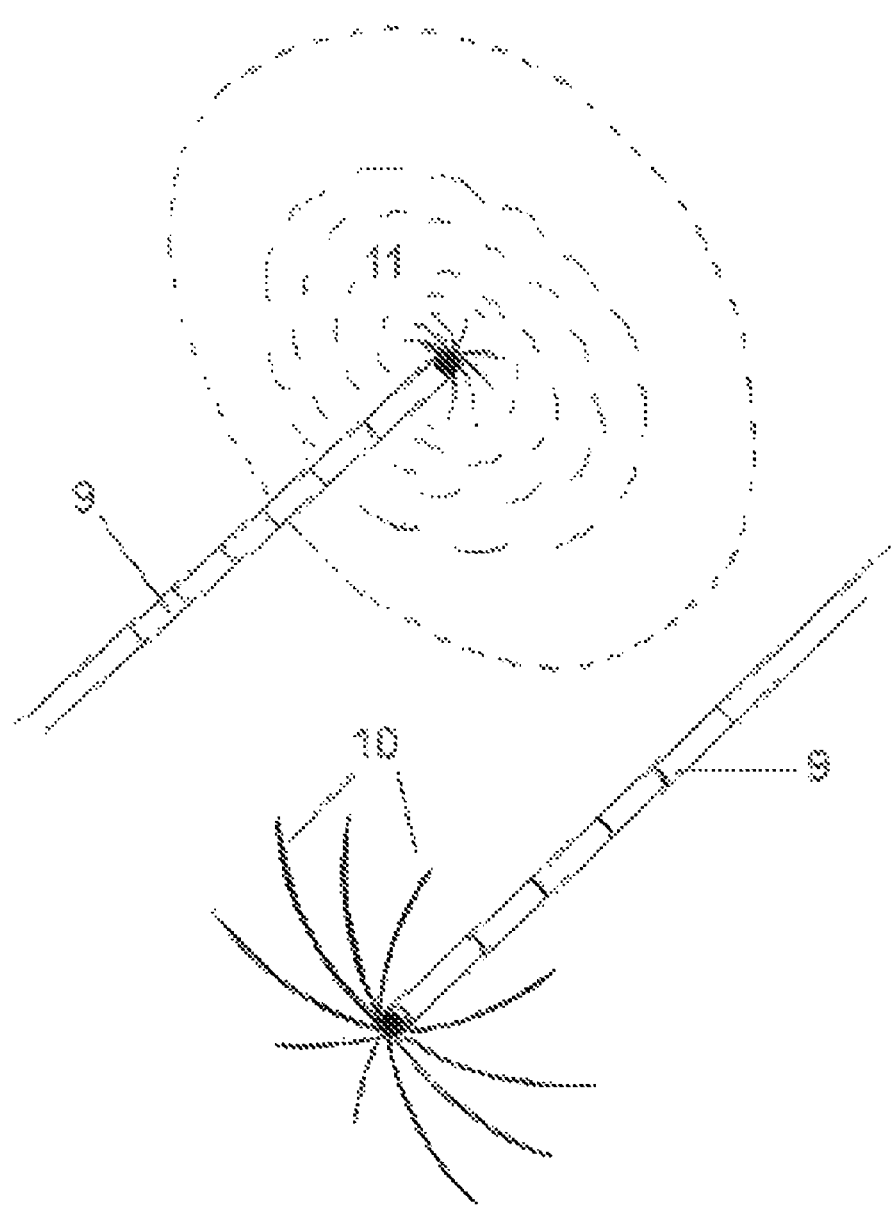
FIG. 3 is an illustration of the ground electrode of the present invention.

FIG. 3 is an illustration of the ground electrode 9 of the present disclosure. As shown in FIG. 3, the ground electrode 9 is inserted into the tumor 11. Also shown in FIG. 3, in some aspects, the ground electrode 9 may have multiple prongs 10 to distribute the electrical pathway throughout the tumor 11.

Figure 4:
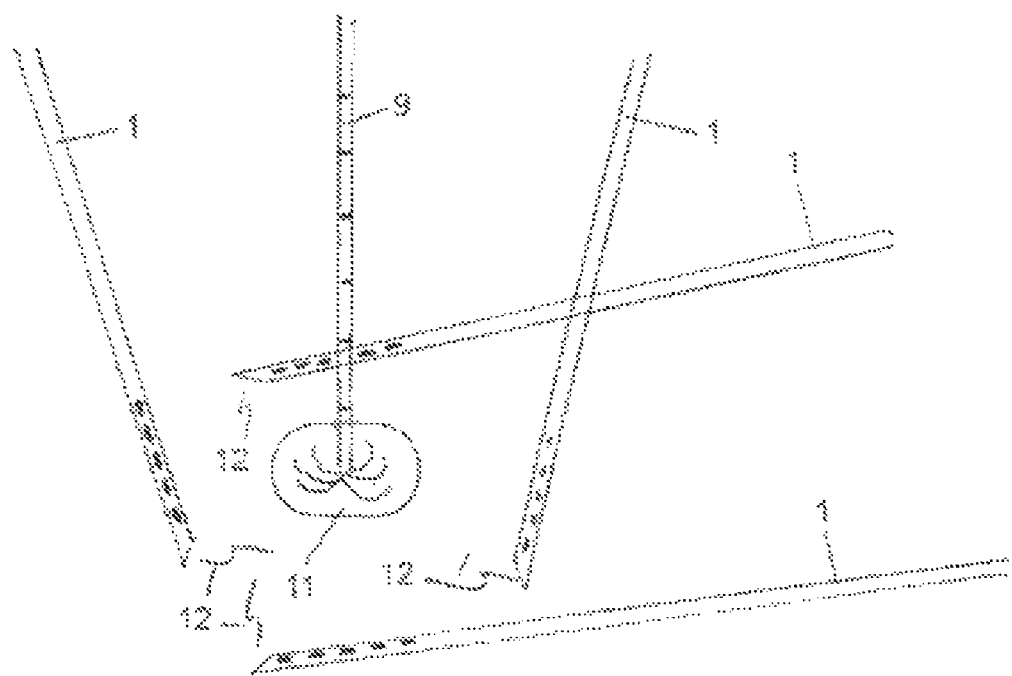
FIG. 4 is an illustration of the ground electrode and multiple hollow electrodes in one embodiment of the present invention.

FIG. 4 is an illustration of the ground electrode 9 and multiple hollow electrodes 1 in one embodiment of the present disclosure. As shown in FIG. 4, the ground electrode 9 is inserted into the tumor 11, and multiple hollow electrodes 1 are inserted in the surrounding tissue through which the chemotherapeutic agent 12 can be released.

Figure 5:
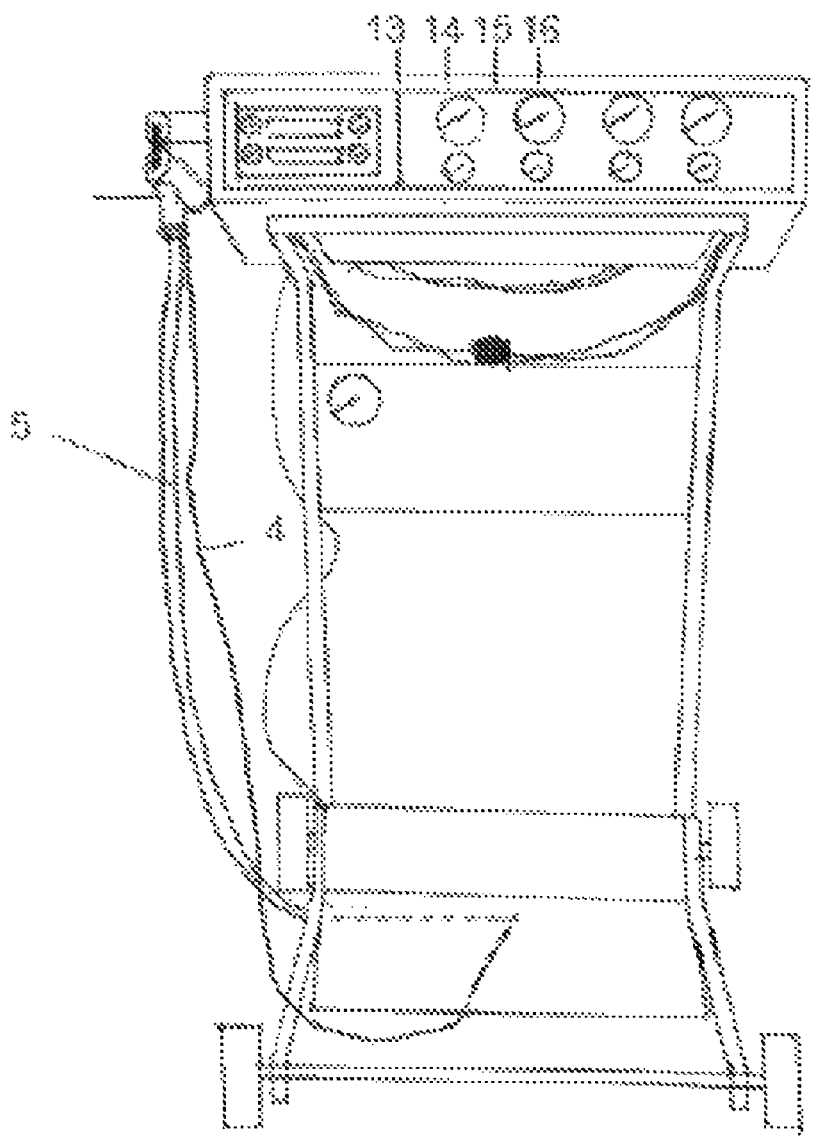
FIG. 5 is an illustration of the complete apparatus of the present invention.

FIG. 5 is an illustration of the complete apparatus of the present invention. As shown in FIG. 5, the computer 13, power supply 14, and pump 15 are all contained within the control unit 16 which is attached to the manipulator 2 by electrical connection 5 and fluid line 4.

While the invention has been illustrated and described in detail in the drawings and foregoing description, the same is to be considered as illustrative and not restrictive in character. Only certain embodiments have been shown and described, and all changes, equivalents, and modifications that come within the spirit of the invention described herein are desired to be protected. Any experiments, experimental examples, or experimental results provided herein are intended to be illustrative of the present invention and should not be considered limiting or restrictive with regard to the invention scope. Further, any theory, mechanism of operation, proof, or finding stated herein is meant to further enhance understanding of the present invention and is not intended to limit the present invention in any way to such theory, mechanism of operation, proof, or finding.

Thus, the specifics of this description and the attached drawings should not be interpreted to limit the scope of this invention to the specifics thereof. Rather, the scope of this invention should be evaluated with reference to the claims appended hereto. In reading the claims it is intended that when words such as "a", "an", "at least one", and "at least a portion" are used there is no intention to limit the claims to only one item unless specifically stated to the contrary in the claims. Further, when the language "at least a portion" and/or "a portion" is used, the claims may include a portion and/or the entire items unless specifically stated to the contrary. Likewise, where the term "input" or "output" is used in connection with an electric device or fluid processing unit, it should be understood to comprehend singular or plural and one or more signal channels or fluid lines as appropriate in the context. Finally, all publications, patents, and patent applications cited in this specification are herein incorporated by reference to the extent not inconsistent with the present disclosure as if each were specifically and individually indicated to be incorporated by reference and set forth in its entirety herein.

We claim:

1. An apparatus for treating solid tumors comprising:
   a. at least one hollow needle having at least one perforation,
   b. at least one ground electrode,
   c. a pump for delivering a chemotherapeutic agent through the perforation in the hollow needle, and
   d. one or more power supplies connected to the hollow needle and the ground electrode capable of delivering:
      i. a pulse of alternating current between the hollow needle and the ground electrode of at least 1000 volts and no more than 1 millisecond duration,
      ii. a direct current between the hollow needle and the ground electrode. between about 1 mA and 1 00 mA, and
      iii. a second alternating current having a frequency range between about 1 MHz and 1 000 MHz.

2. The apparatus of claim 1 wherein the ground electrode is one or more needle.

3. The apparatus of claim 1 further comprising an ultrasound imager.

4. The apparatus of claim 1 comprising a manipulator housing the at least one hollow needle.

5. The apparatus of claim 3 wherein the manipulator further comprises a servo drive for injecting the hollow needle into the tissue.

6. The apparatus of claim 4 wherein the servo drive is connected to a trigger on the manipulator.

7. The apparatus of claim 5 the servo drive in the manipulator is connected to a computer.

8. A method for treating solid tumors comprising the steps of:
   a. injecting at least one hollow needle having at least one perforation into a tissue adjacent to a solid tumor,
   b. placing at least one ground electrode within or adjacent to the solid tumor,
   c. pumping a chemotherapeutic agent through the perforation in the hollow needle, and
   d. providing a pulse of alternating current between the hollow needle and the ground electrode of at least 1000 volts and no more than 1 millisecond duration, a direct current between the hollow needle and the ground electrode between about 1 milliamp and 100 milliamps, and a second alternating current having a frequency range between about 1 MHz and 1000 MHz.

9. The method of claim 8 wherein the ground electrode is provided as one or more needles injected into the tissue.

10. The method of claim 8 further comprising the step of monitoring the injection of the hollow needle using an ultrasound imager.

11. The method of claim 8 further comprising the step of providing a manipulator that houses the hollow needle.

12. The method of claim 11 wherein a servo drive is further provided in the manipulator for injecting the hollow needle into the tissue.

13. The method of claim 12 wherein a trigger is further provided to control the servo drive on the manipulator.

14. The method of claim 13 where the servo drive in the manipulator is connected to a computer.

* * * * *